United States Patent [19]

Sauer et al.

[11] Patent Number: 5,431,666
[45] Date of Patent: Jul. 11, 1995

[54] SURGICAL SUTURE INSTRUMENT

[75] Inventors: Jude S. Sauer, Pittsford; Mark A. Bovard, Williamson; Roger J. Greenwald, Holley; John F. Hammond, Canandaigua; James W. Kaufer, Pittsford, all of N.Y.

[73] Assignee: LaserSurge, Inc., Rochester, N.Y.

[21] Appl. No.: 201,296

[22] Filed: Feb. 24, 1994

[51] Int. Cl.[6] .............................................. A61B 17/04
[52] U.S. Cl. .................................... 606/139; 606/144
[58] Field of Search ........................... 606/144–148, 606/139; 112/169, 104

[56]       References Cited
       U.S. PATENT DOCUMENTS

| | | |
|---|---|---|
| 2,269,963 | 1/1942 | Wappler . |
| 4,109,658 | 8/1978 | Hughes . |
| 4,493,323 | 1/1985 | Abright et al. .................. 606/139 |
| 4,635,637 | 1/1987 | Schreiber . |
| 4,738,255 | 4/1988 | Goble et al. . |
| 4,741,330 | 5/1988 | Hayhurst . |
| 4,926,860 | 5/1990 | Stice et al. ..................... 606/144 |
| 4,981,149 | 1/1991 | Yoon et al. . |
| 5,037,422 | 8/1991 | Hayhurst et al. . |
| 5,046,513 | 9/1991 | Gatturna et al. . |
| 5,085,661 | 2/1992 | Moss . |
| 5,304,184 | 4/1994 | Hathaway et al. ............. 606/144 |

Primary Examiner—Gary Jackson

[57] ABSTRACT

A surgical apparatus, method of use and instrumentation kit are provided for suturing body tissue. The apparatus includes a handle assembly and an elongated body assembly detachably engaged to the handle assembly. The elongated body assembly includes an actuating mechanism for sequentially pulling the first and second ferrule portions of a length of suture material through body tissue. The length of suture material and the first and second ferrule portions are releasably retained in the elongated body assembly. The instrumentation kit includes the surgical apparatus and at least one additional elongated body assembly in an enclosure.

21 Claims, 9 Drawing Sheets

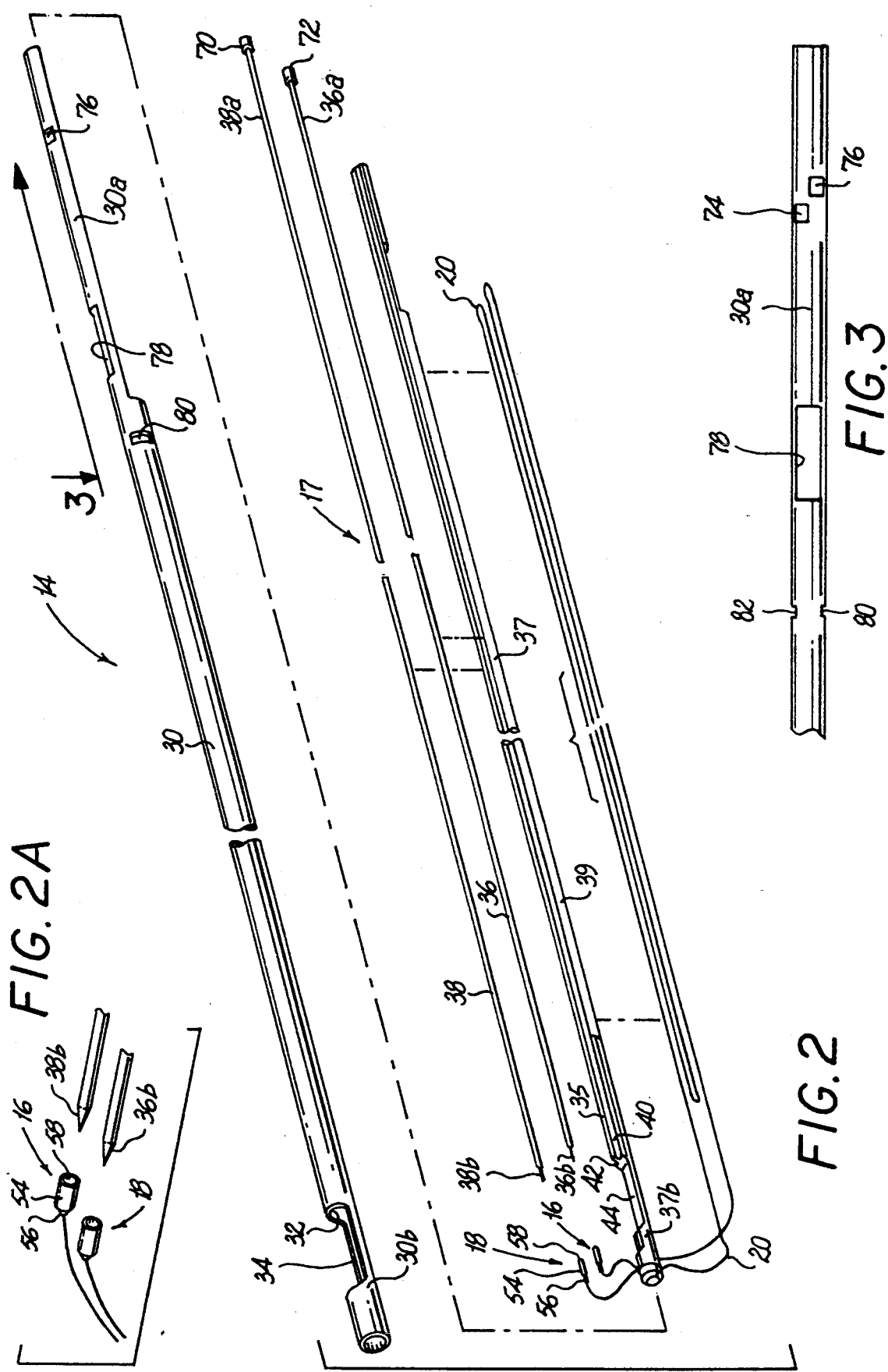

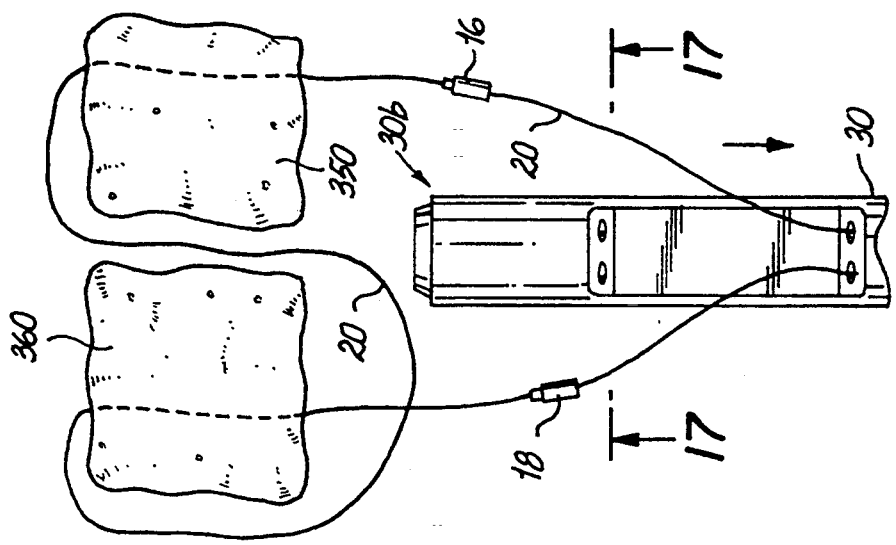
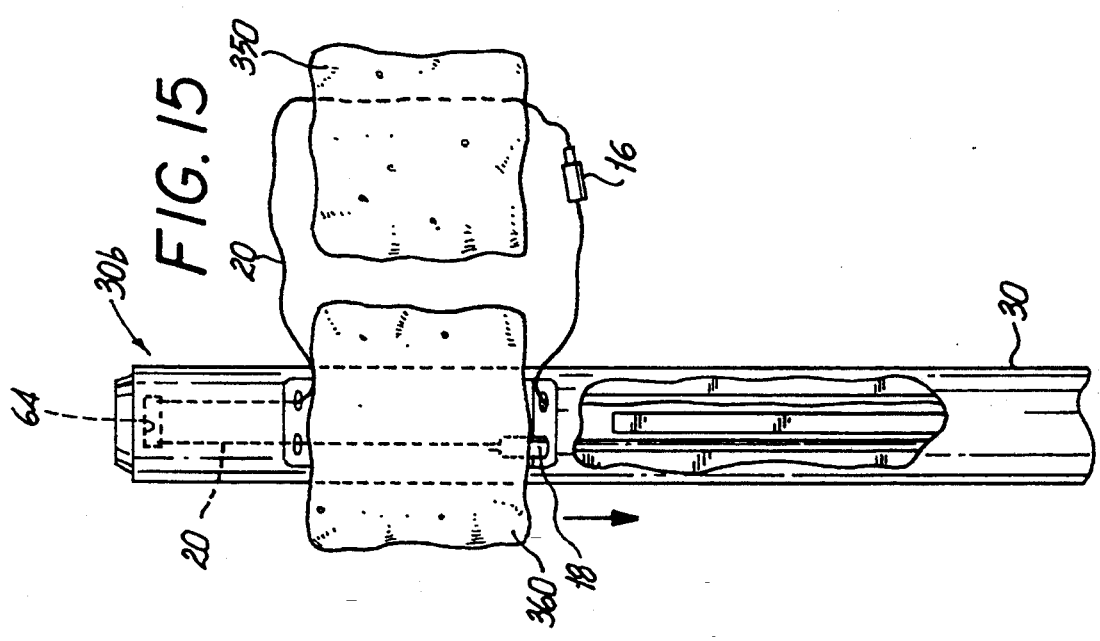
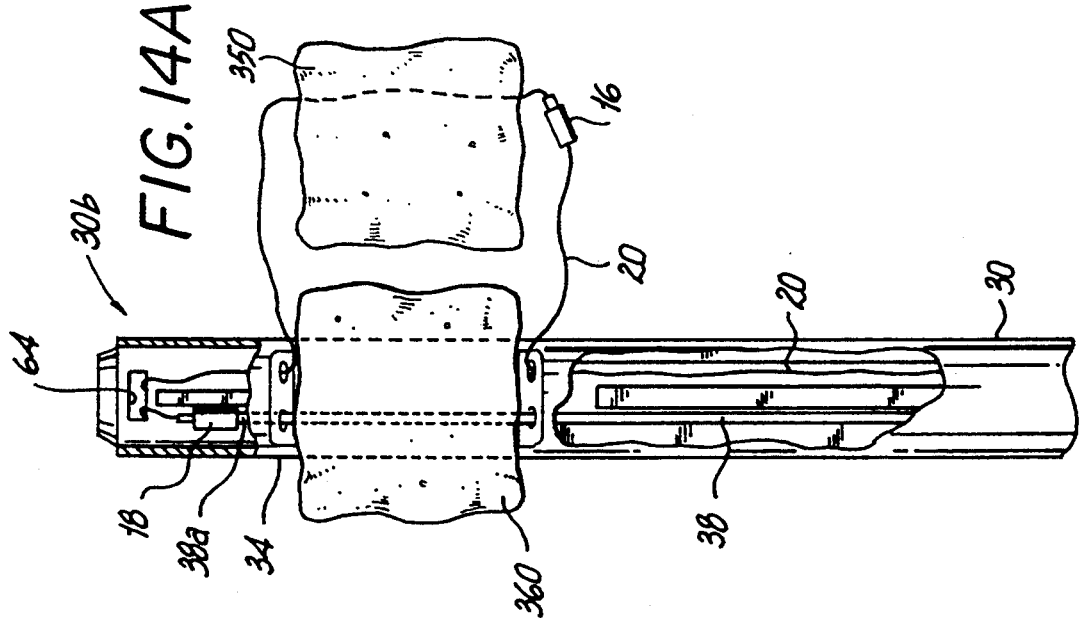

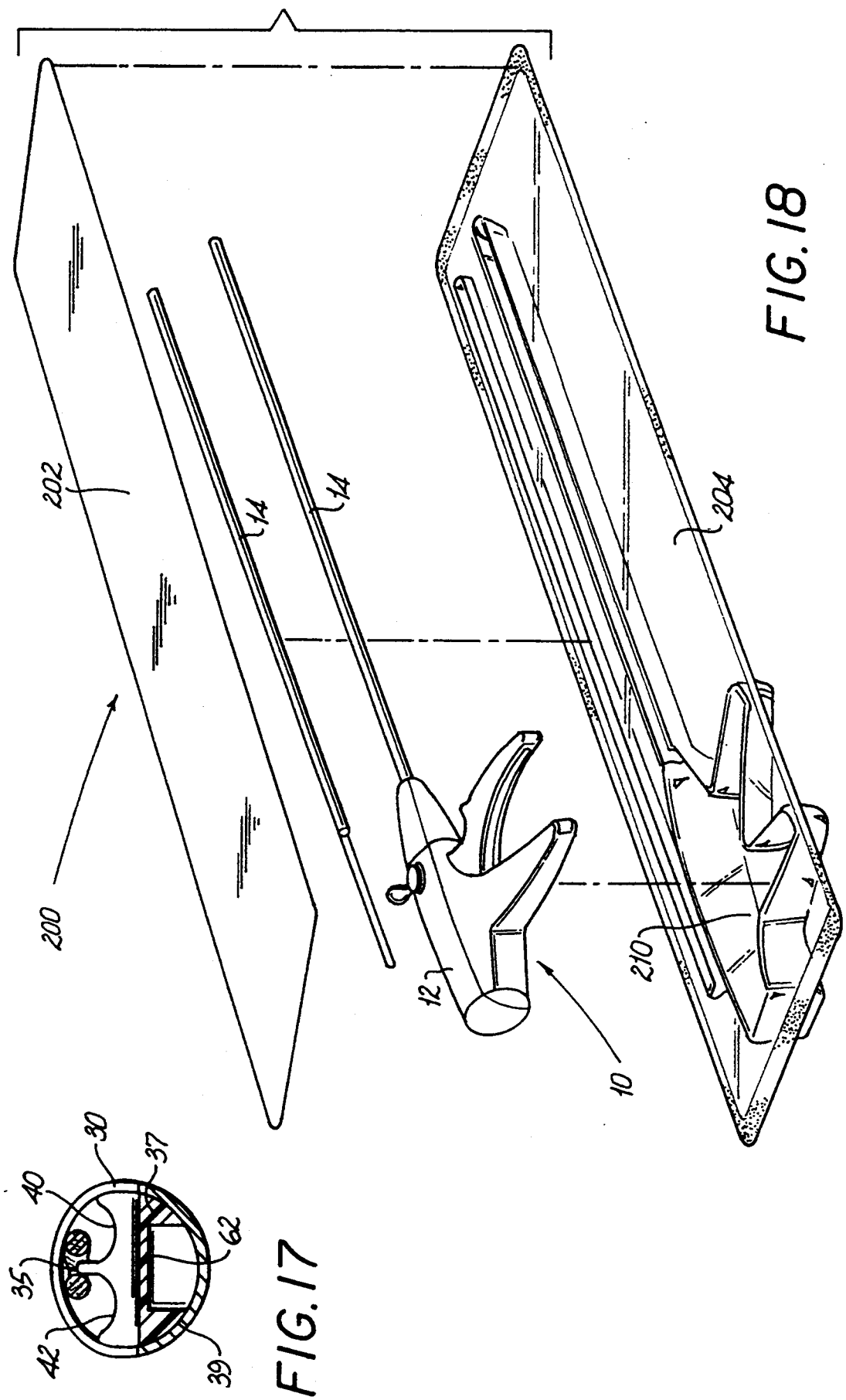

SURGICAL SUTURE INSTRUMENT

BACKGROUND OF THE INVENTION

1. Field of the Invention

The subject invention relates to an endoscopic or laparoscopic surgical apparatus, and more particularly to a surgical apparatus having a disposable elongated body assembly for passing a length of suture material through bodily tissue or organ parts.

2. Description of Related Art

The recent advancement of minimally-invasive surgical procedures has proven to be an advantageous alternative over prior invasive surgical procedures. Advantages gained by minimally-invasive surgical procedures include quicker recovery time as well as the reduction in the length of hospital stays and medical costs.

Generally, endoscopic surgery involves incising through body walls, for example, viewing and/or operating on the ovaries, uterus, gall bladder, bowels, kidneys, appendix, etc. There are many common endoscopic surgical procedures, including arthroscopy, laparoscopy (pelviscopy), and gastroentroscopy, for example. Typically, a trocar assembly is utilized for creating the incisions through which the endoscopic surgery is performed. The trocar assembly includes a sharp pointed obturator which is used to puncture and penetrate the skin and surrounding tissue to reach the surgical site. The obturator is positioned within a cannula which is generally configured as a sleeve member. The cannula remains in place after the obturator has been removed and provides a path for the insertion of surgical equipment needed for the particular surgical procedure.

Prior to introducing the cannula through the body wall, the surgeon may insufflate the body cavity with insufflation gas, typically through a Verres needle or like device. Insufflation expands the body cavity creating an enlarged free area between internal body organs and the body wall. The surgeon is then able to introduce cannulas through the body wall so as to create a port of entry for surgical instrumentation.

Typically, a camera or endoscope is inserted through a cannula thereby enabling the visual inspection and magnification of the body cavity. With the visual assistance of an endoscope and external television monitor, the surgeon can perform diagnostic and therapeutic procedures at the surgical site with aid of specialized instrumentation, such as, graspers, dissectors, clip appliers, lasers, electrocautery devices and the like which are specifically designed for introduction and manipulation through additional cannulas.

Thus, instead of a large incision (typically 12 inches or larger) that cuts through major muscles, patients undergoing endoscopic surgery receive more cosmetically appealing incisions, which are typically between 5 and 10 millimeters in size. Recovery is, therefore, much quicker. In addition, because the surgical field is greatly magnified, surgeons are better able to dissect blood vessels and control blood loss.

In many endoscopic surgical procedures, including those involved in endoscopic surgery, it is often necessary to suture bodily organs or tissue and thereafter knot the suture material so as to approximate or adjoin tissue pieces. This procedure is especially challenging during endoscopic surgery because of the small openings through which the suturing of the bodily organs or tissues must be accomplished.

In the past, suturing of bodily organs or tissue through endoscopic surgery was achieved through the use of a sharp metal suture needle attached to an end of a length of suture material. In a typical endoscopic surgical procedure, the surgeon grasps the suture needle with an endoscopic grasping instrument, enabling the suture needle to be introduced into the abdominal body cavity of the patient, via a cannula. Through manipulation of the grasping instrument, the surgeon effects the suture needle to penetrate and pass through bodily tissue pulling the suture material therethrough.

However, during endoscopic surgery, the above described procedure of passing a length of suture material through first and second tissue pieces is time consuming and burdensome due to the difficult maneuvers and manipulations which are required through the small endoscopic openings.

There have been many attempts to provide devices to facilitate suturing during endoscopic surgery. Such devices include staples, clips, clamps or other fasteners as disclosed in U.S. Pat. Nos. 4,041,129 to Hayhurst et al., 5,080,663 to Mills et al., 5,021,059 to Kensy et al., 4,841,888 to Mills et al., 4,741,330 to Hayhurst, 4,724,840 to McVay et al., 4,705,040 to Mueller et al., 4,669,473 to Richards et al., 4,627,437 to Bedi et al., 4,448,194 to DiGiovanni et al., 4,039,078 to Bone, 4,235,238 to Ogiv et al., 4,006,747 to Kronenthal et al., 3,875,648 to Bone and 5,085,661 to Moss. However, none of the above listed devices overcome the aforementioned disadvantages associated with suturing body tissue.

There is, accordingly, a need for a new and improved suture apparatus, particularly useful in endoscopic surgery to overcome the shortcomings and drawbacks of the above-mentioned apparatus.

SUMMARY OF THE INVENTION

The present invention provides a novel surgical apparatus for suturing body tissue pieces together, and more particularly, to a surgical apparatus for passing the opposed ends of a length of suture material into body tissue pieces which are to be adjoined or approximated together. The body tissue pieces may be adjoined or approximated through the tensioning of the length of suture material which has been passed through the body tissue pieces.

The surgical apparatus of the present invention includes a handle assembly, an elongated body assembly extending distally from the handle assembly, and a suture positioned in the body assembly. The apparatus further includes at least one needle positioned in the body assembly spaced from the suture and an actuating mechanism for moving the needle into engagement with the suture.

In a method of use, first the surgeon inserts the distal end portion of the apparatus into the body cavity and positions that end portion adjacent a first piece of tissue. The surgeon then pierces the first piece of tissue and pulls a first end of the suture through the tissue. The surgeon then positions the distal end of the instrument adjacent a second piece of tissue without removing the instrument from the body cavity and pierces that second piece of tissue, pulling a second end of suture through the second piece of tissue.

Additionally, the present invention provides a surgical instrumentation kit which makes available the necessary equipment for performing a surgical procedure utilizing numerous elongated body assemblies with a single handle assembly.

The surgical apparatus, method of use and instrumentation kit of the present invention are particularly adapted for use during endoscopic surgical techniques. However, it is to be appreciated that the surgical instrument, method of use and instrumentation kit of the present invention can be utilized during other operative procedures requiring the usage of a surgical apparatus to suture bodily tissue or organ parts.

BRIEF DESCRIPTION OF THE DRAWINGS

Further features of the present invention will become more readily apparent from the following detailed description of the invention taken in conjunction with the accompanying drawings described hereinbelow, in which:

FIG. 2 is an exploded perspective view of the elongated body assembly of the surgical apparatus of FIG. 1;

FIG. 2A is an enlarged view of the needles and ferrules of FIG. 2;

FIG. 3 is a top elevational view of the proximal end portion of the outer tubular member of FIG. 2;

FIG. 14a is a top elevational view in partial cutaway of the distal end portion of the elongated body assembly illustrated in FIG. 15, wherein the second needle has engaged the second ferrule portion;

FIG. 15 is a top elevational view in partial cutaway of the distal end portion of the elongated body assembly illustrated in FIG. 14, wherein the second ferrule portion and attached length of suture material have moved proximally through a second tissue piece;

FIG. 16 is a top elevational view of the distal end portion of the elongated body assembly illustrated in FIG. 15, wherein the length of suture material is being released outward from the tissue receiving portion of the elongated body assembly and is fastened to the first and second tissue pieces with, respectively, the first and second ferrule portions;

FIG. 17 is a cross-sectional view taken along line 17—17 of FIG. 16; and

FIG. 18 is a perspective view illustrating the packaging device for the instrumentation kit of the present invention.

DETAILED DESCRIPTION OF THE PREFERRED EMBODIMENTS

Figure 1:
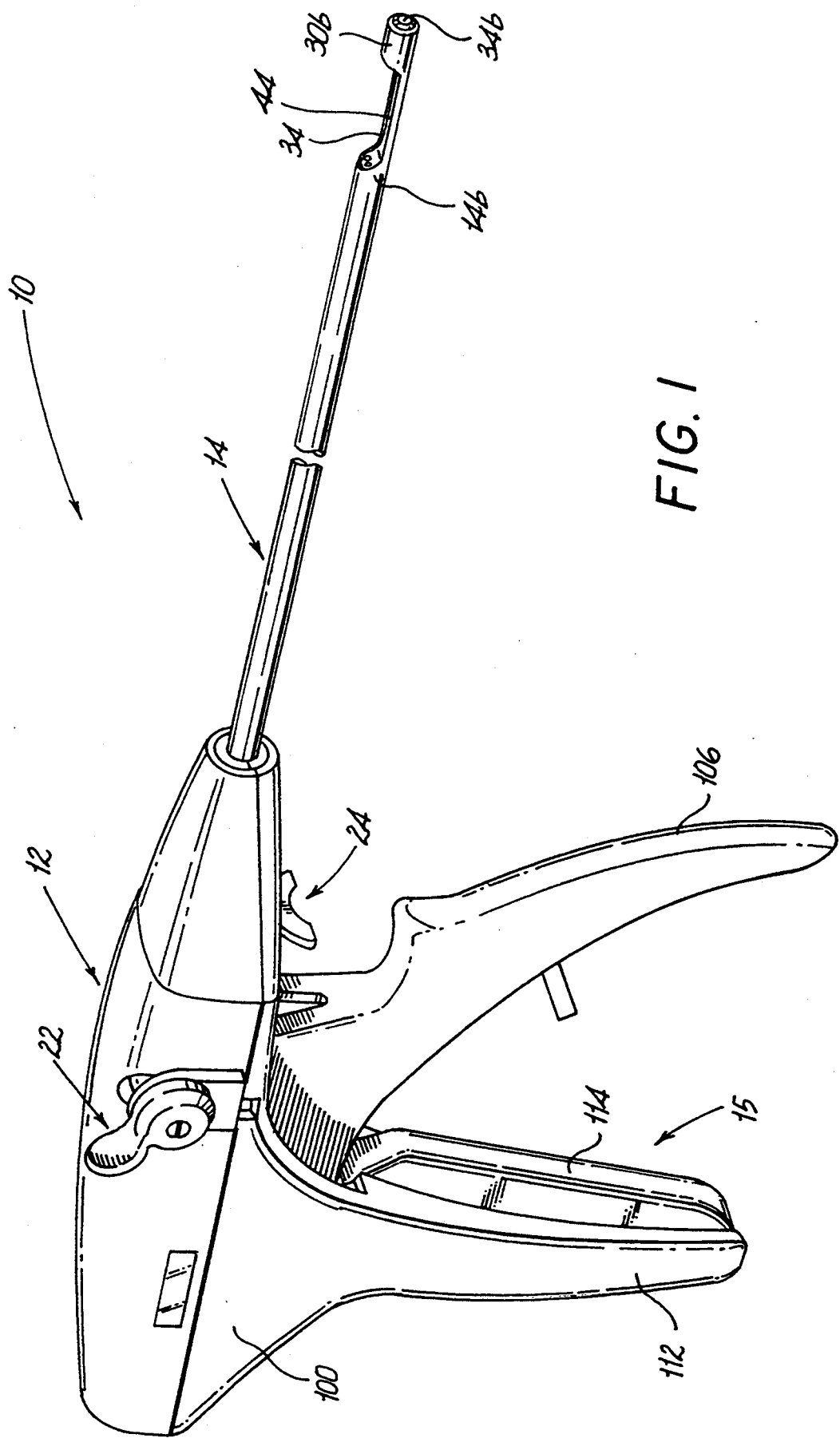
FIG. 1 is a perspective view of a surgical apparatus of the present invention.

Because endoscopic procedures are more common than laparoscopic procedures, the present invention shall be discussed in terms of endoscopic procedures and apparatus. However, use herein of terms such as "endoscopic", "endoscopically", and "endoscopic portion", among others, should not be construed to limit the present invention to apparatus for use only in conjunction with an endoscopic tube. To the contrary, it is believed that the present invention may find use in procedures wherein access is limited to a small incision, such as, for example, arthroscopic procedures.

In the drawings and in the description which follow, the term "proximal", as is traditional, will refer to the end of the surgical apparatus of the present invention which is closest to the operator, while the term "distal" will refer to the end of the apparatus which is furthest from the operator.

Referring now in specific detail to the drawings, in which like reference numerals identify similar or identical elements, FIG. 1 illustrates a surgical apparatus shown generally at 10. The surgical apparatus 10 comprises a handle assembly 12 having actuation structure 15 and an elongated body assembly 14 extending distally from the handle assembly 12 and defining a longitudinal axis thereof. The elongated body assembly 14 is preferably dimensioned for endoscopic utilization. An actuating mechanism 17, as illustrated in FIG. 2, is operatively disposed within the elongated body assembly 14 and operatively associated with the actuation structure 15 of the handle assembly 12 for sequentially pulling first and second needle receiving or ferrule portions 16 and 18 connected to a length of suture material 20 from a distal end portion 14b of the elongated body assembly 14 and through body tissue. A switching mechanism 22 is operatively associated with the handle assembly 12 for enabling the actuating mechanism 17 to sequentially pull the first and second ferrule portions 16 and 18 through body tissue. The elongated body assembly 14 and handle assembly 12 are dimensioned and configured such that the elongated body assembly 14 is engaged with the handle assembly 12. Alternately, the body assembly 14 can be permanently attached to the handle assembly 12. A locking assembly 24 is operatively associated with the handle assembly 12 for securing the engagement between the handle assembly 12 and the elongated body assembly 14.

The components of the elongated body assembly 14 of the surgical apparatus 10 are best illustrated in FIG. 2. The elongated body assembly 14 includes an outer tubular member 30 defining a bore 32 therethrough within which the components of the actuating mechanism 17 are positioned. A tissue receiving cutout portion 34 is defined at a distal end portion 30b of the outer tubular member 30 and is dimensioned and configured for reception of a tissue piece, the significance of which will be described in further detail below.

The actuating mechanism 17 includes an elongated insert member 37 and first and second elongated needle members 36 and 38. The elongated insert member 37 is received within the bore 32 of the outer tubular member 30 such that the distal end 37b of elongated insert member 37 is disposed adjacent the distal end 30b of the outer tubular member 30, as best shown in FIG. 1. The top portion 35 of the elongated insert member 37 defines first and second elongated guide channels 40 and 42, preferably formed parallel to one another and dimensioned and configured for slidable reception, respectively, of the first and second elongated needle members 36 and 38. Further, the distal end portion 37b of the elongated insert member 37 also defines a tissue receiving cutout portion 44 which is disposed in alignment with the tissue receiving cutout portion 34 of the outer tubular member 30 (FIG. 1).

The first and second elongated needle members 36 and 38 are configured for reciprocating coaxial movement between a distalmost position and a proximal most position in the outer tubular member 30. Each respective elongated needle member 36 and 38 is preferably fabricated from a resilient material, such as piano wire. The distal end portion of each respective elongated needle member 36 and 38 is provided with a sharpened distal end 36b and 38b configured to pierce through a body tissue piece received in the tissue cutout portions 34 and 44 and engage a respective ferrule portion 16 and 18 releasably retained in the distal end 37b of the elongated insert member 37. During proximal coaxial movement, each sharpened end 36b and 38b of each respective elongated needle member 36 and 38 is configured to pull a respective ferrule portion 16 and 18 through a tissue piece. The procedure of pulling each respective ferrule portion 16 and 18 through a piece of body tissue will be described in further detail below.

Still referring to FIG. 2, the first and second ferrule portions 16 and 18 are releasably retained in a distal end portion 37b of the elongated insert member 37 in coaxial alignment respectively with the first and second elongated needle members 36 and 38. In one embodiment, the ferrules 16, 18 have an inner diameter slightly smaller than the outer diameter of the sharpened ends of the needles 36b and 38b. In either embodiment, when the sharpened ends 36b, 38b are inserted into the ferrules 16 and 18, friction holds the ferrule onto the sharpened end. An anti-reverse mechanism can also be included to prevent the needle from being retracted until it had been completely inserted into the ferrule, thus preventing partial insertion of the needle into the ferrule.

Referring to FIG. 2A, each first and second ferrule portion 16 and 18 includes a cylindrical body portion 54 defining a bore therethrough having a closed end 56 and an opposing open end 58. Clearly, other shapes and configurations of the needle-receiving portion are contemplated. Each open end 58 is dimensioned and configured for detachable slidable reception of the sharpened distal end portions 36b and 38b of each respective elongated needle member 36 and 38. Each first and second ferrule portion 16 and 18 is releasably retained in the distal end 37b of the elongated insert member 37, as mentioned above, and the closed end 56 of each respective ferrule portion 16 and 18 is fastened to a length of suture material 20 by, for example, swaging the ferrule onto the suture. The length of suture material 20 is releasably retained in an elongated disposable channel 62 defined on the bottom portion 39 of the elongated insert member 37 as best illustrated in FIG. 17. The length of suture material 20 slidably extends through an aperture 64 (shown in phantom in FIG. 15) defined at the distal end 37b of the elongated insert member 37 so as to fasten to each respective ferrule portion 16 and 18 releasably retained in the distal end portion 37b of the elongated insert member 37.

Each respective ferrule portion 16 and 18, and the length of suture material 20, are fabricated from a biocompatible material and are preferably formed of conventional non-bioabsorbable materials. Alternatively, each respective ferrule portion 16 and 18, and the length of suture material 20, may be fabricated from a bioabsorbable polymer comprising a homopolymer, copolymer or a blend obtained from one or more monomers selected from the group consisting of glycolide, glycolic acid, lactide, lactic acid, p-dioxanone, E-caprolactone and trim ethylene carbonate.

Referring now to FIGS. 2 and 3, the proximal end 36a and 38a of each elongated needle member 36 and 38 is respectively provided with an enlarged locking detent 70 and 72 for facilitating the detachable engagement between the actuation structure 15 (FIG. 4) of the handle assembly 12 and each respective elongated needle member 36 and 38. First and second cutout portions 74 and 76 configured for reception of each respective enlarged locking detent 70 and 72 are defined in the proximal end portion 30a of the outer tubular member 30 along the longitudinal axis of travel of each respective elongated needle member 36 and 38. When each respective elongated needle member 36 and 38 is in disengagement with the actuation structure 15 of the handle assembly 12, each respective enlarged locking detent 70 and 72 is biased upwards into each respective cutout portion 74 and 76 so as to prevent unwanted longitudinal movement of each respective elongated needle member 36 and 38 in the elongated body assembly 14. An elongated cutout portion 78 is further defined at the proximal end portion 30a of the outer tubular member 30 so as to facilitate detachable engagement, via the switching mechanism 22 (FIG. 1), between each respective elongated needle member 36 and 38 and the actuation structure 15 of the handle assembly 12, which will be further described below.

Still referring to FIGS. 2 and 3, a pair of locking channels 80 and 82 are defined transverse to the longitudinal axis of the elongated body assembly 14 at the proximal end portion 30a of the outer tubular member 30. The pair of locking channels 80 and 82 are preferably formed parallel to one another and are configured to cooperate with the locking assembly 24 of the handle assembly 12 so as to provide detachable engagement between the outer tubular member 30 and the handle assembly 12 described hereinbelow.

Figure 4:
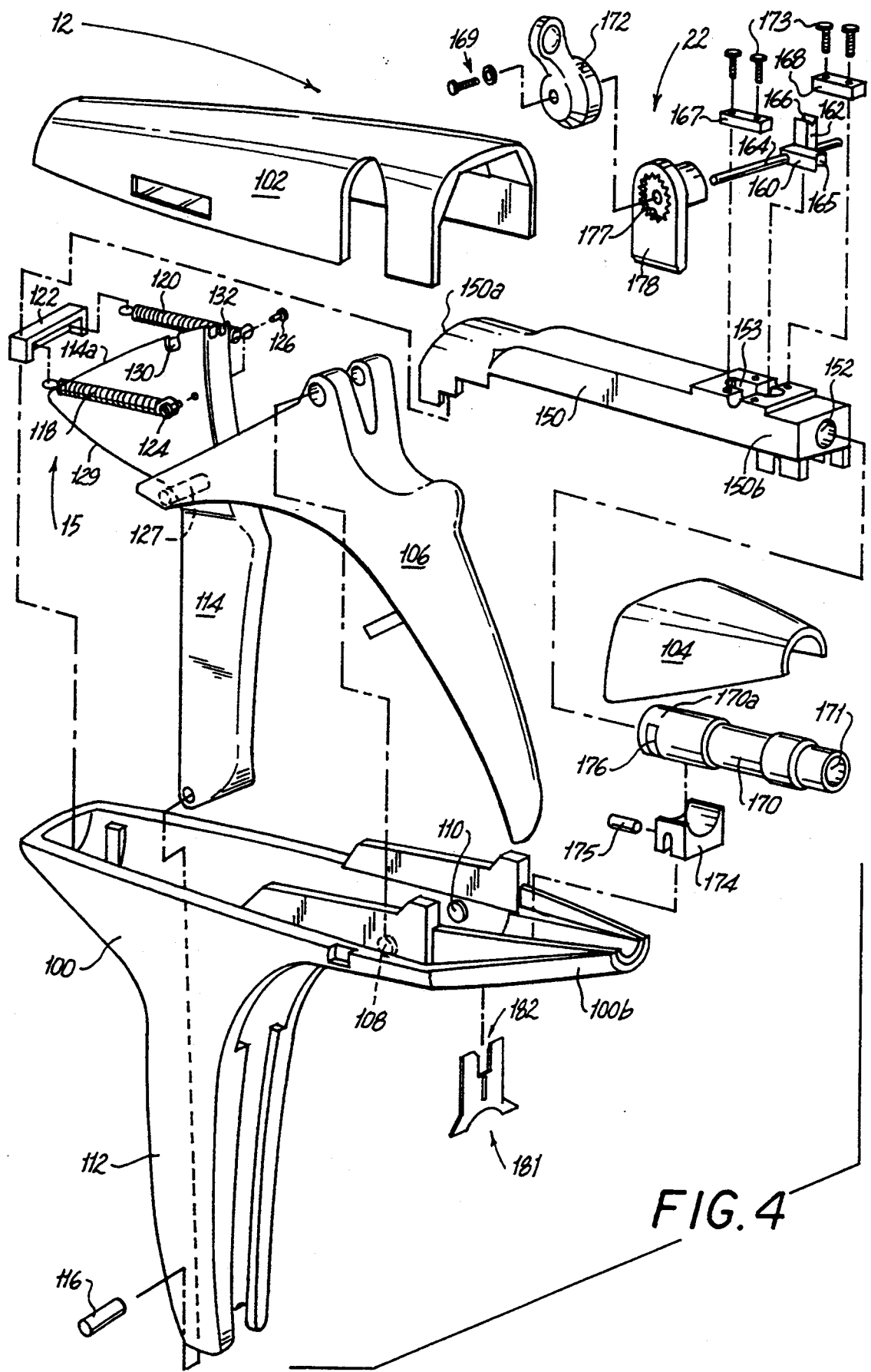
FIG. 4 is an exploded perspective view of the handle assembly of the surgical apparatus of FIG. 1.

Referring now to FIG. 4, the handle assembly 12 includes a body portion 100 and first and second top cover portions 102 and 104 within which the components of the handle assembly 12 are positioned. The handle assembly 12 further includes a pivotable handle member 106 pivotably mounted to body portion 100 by mounting detents 108 and 110. The pivotable handle member 106 is movable in approximation to a stationary grip portion 112 defined by the body portion 100 so as to actuate the actuation structure 15 of the handle assembly 12, thereby effecting remote actuation of the actuating mechanism 17 in the elongated body assembly 14 (FIG. 2).

The actuation structure 15 includes an elongated drive arm member 114 operatively associated with the pivotable handle member 106 and pivotably connected to the lower end of the stationary handle member 112 by pivot pin 116. A pair of handle springs 118 and 120 extending from a mounting bar 122 fastened to the distal end of the body portion 100 are connected to the drive arm member 114 through mounting pins 124 and 126 so as to bias the operatively associated pivotable handle member 106 to an open position. A cam roller member 127 (shown in phantom in FIG. 4) is rotatably mounted to the pivotable handle member 106 and is configured to move along a cam path 129 defined on the drive arm member 114 thereby effecting corresponding movement of the drive arm member 114 between a distal and proximal position.

Figure 7:
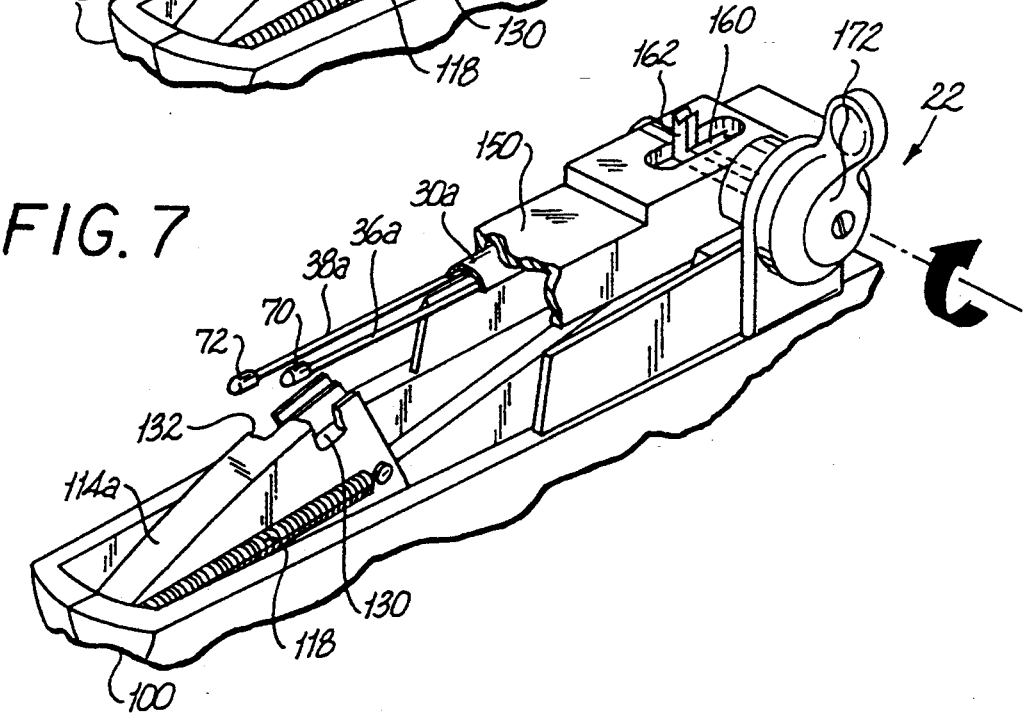
FIG. 7 is a partial perspective view of the top portion of the handle assembly wherein the switching mechanism is positioned in a third position such that neither the first nor second elongated needle member is engaged with the drive arm member of the handle assembly.

Referring to FIGS. 4 and 7, the top portion 114a of the elongated drive member 114 defines first and second cutout portions 130 and 132 which are dimensioned and configured to retain, respectively, the enlarged locking detents 70 and 72 of the first and second elongated needle members 36 and 38, such that, reciprocating movement of the drive arm member 114 effects corresponding reciprocating coaxial movement of a detachably retained elongated needle member 36 or 38. The switching mechanism 22 is operably mounted to an elongated guide block 150 in the handle assembly 12 to effect selective sequential detachable retainment of the enlarged locking detents 70 and 72 of the first and second elongated needle members 36 and 38 in the respective cutout portions 130 and 132 of the elongated drive arm member 114, described hereinbelow.

The elongated guide block 150 is mounted in the distal end portion 100b of the body 100 of the handle assembly 12 and includes an open proximal end 150a and an aperture 152 defined at the distal end 150b thereof. The aperture 152 is configured for slidable reception of the proximal end portion 30a of the outer tubular member 30, such that, with the proximal end portion 30a of the outer tubular member 30 fully received in the aperture 152, the enlarged locking detents 70 and 72 of the elongated needle members 36 and 38 releasably retained in the respective cutout portions 74 and 76 (FIG. 2) of the outer tubular member 30 are in alignment with the respective first and second cutout portions 130 and 132 of the elongated drive arm member 114, as best illustrated in FIG. 7. Further, the top portion of the elongated guide block 150 defines a through slot 152 which is in alignment with the elongated engaging cutout portion 78 of the outer tubular member 30 so as to facilitate sequential detachable engagement between the switching mechanism 22 and each respective elongated needle member 36 and 38.

The switching mechanism 22 is mounted to the top portion of the elongated guide block 150 and includes first and second camming members 160 and 162 preferably oriented perpendicular to one another and defining a respective curved surface portion 165 and 166 for cooperatively interacting with the proximal end portions 36a and 38a of the respective elongated needle members 36 and 38. The camming members 160 and 162 are fixed to a rotatable rod member 164 and are mounted in alignment with the through slot 152 of the elongated guide block 150. The rotatable rod member 164 is rotatably mounted to the top portion of the elongated guide block 150 through mounting plates 167 and 168 affixed to the elongated guide block 150 through mounting screws 173. A rotatable lever arm member 172 is affixed to an end of the rotatable rod member 164 through screw 169. The lever arm member 172 is configured to interact with interengaging ratchet teeth 177 of a rachet mechanism 178 so as to provide for incremental movement of the lever arm member 172 and attached first and second camming members 160 and 162.

Figure 5:
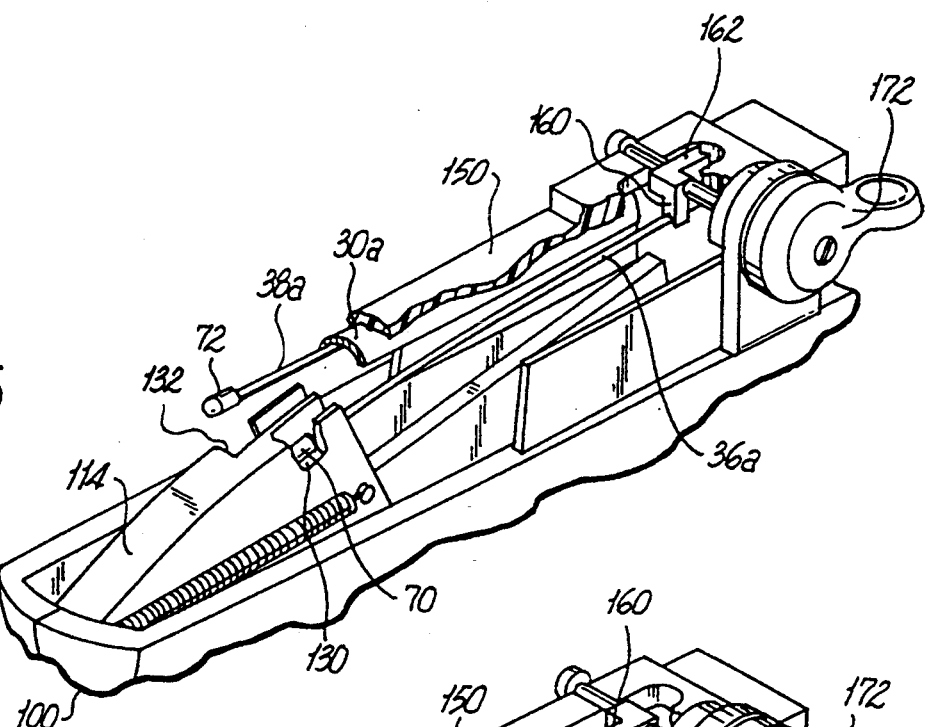
FIG. 5 is a partial perspective view of the top portion of the handle assembly illustrated in FIG. 4, wherein the switching mechanism is positioned in a first position so as to engage the first elongated needle member with the drive arm member of the handle assembly.
Figure 6:
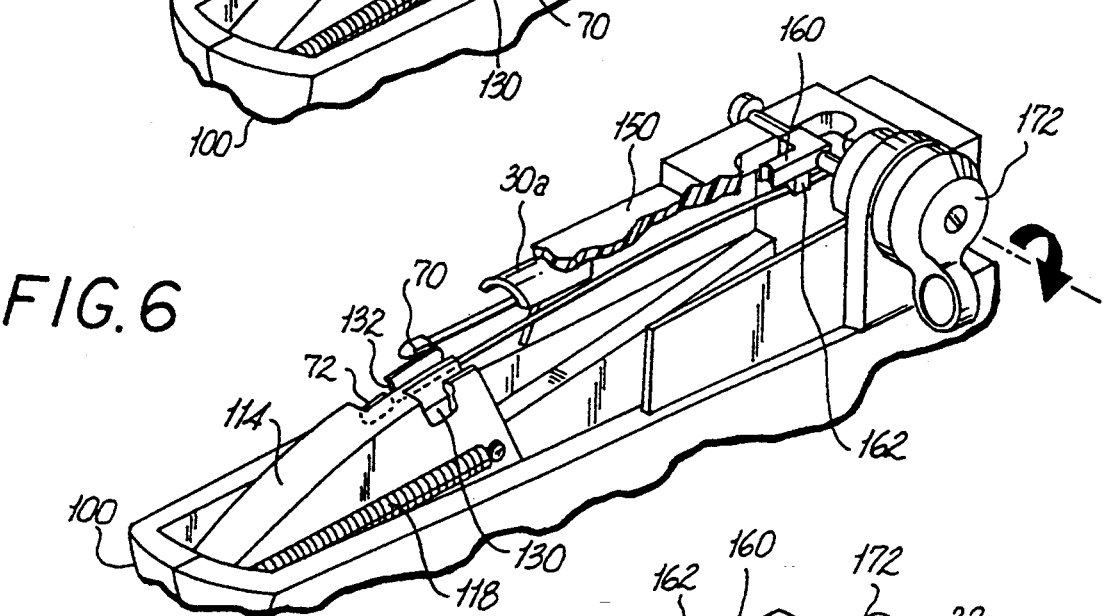
FIG. 6 is a partial perspective view of the top portion of the handle assembly wherein the switching mechanism is positioned in a second position so as to engage the second elongated needle member with the drive arm member of the handle assembly.

Referring to FIGS. 5, 6 and 7, the lever arm member 172 is configured to be movable between three positions. In a first position, as illustrated in FIG. 5, the lever arm member 172 is oriented such that the first camming member 160 is oriented into engagement with the proximal end portion 36a of the first elongated needle member 36 such that the elongated locking detent 70 of the first needle member 36 is releasably retained in the first cutout portion 130 of the elongated drive arm member 114. Thereby, reciprocating movement of the elongated drive arm member 114 effects corresponding reciprocating coaxial movement of the first elongated needle member 36 in the outer tubular member 30 (FIG. 2). In a second position, as illustrated in FIG. 6, the lever arm member 172 is oriented such that the second camming member 162 is oriented into engagement with the proximal end portion 38a of the second elongated needle member 38, such that, the enlarged locking detent 72 of the second needle member 38 is releasably retained in the second cutout portion 132 of the elongated drive arm member 114. Thus, reciprocating movement of the elongated drive arm member 114 effects corresponding reciprocating coaxial movement of the second elongated needle member 38 in the outer tubular member 30. As described above, the positioning of the lever arm member 172 between the first and second positions (FIGS. 5 and 6) enables engagement between the elongated drive arm member 114 and the first and second elongated needle members 36 and 38. In another embodiment, this manual method of selecting the needles can be replaced by an automatic mechanism in which the second needle would automatically be selected after the first needle had been fired.

Referring now to FIG. 7, when the lever arm member 172 is positioned in the third position, neither the first nor second camming members 160 and 162 are engaged with the respective elongated needle members 36 and 38, thereby facilitating the elongated body assembly 14 to engage or disengage from the handle assembly 12. Manipulation of the locking assembly 24 (FIG. 1) provides for the detachable engagement of the handle assembly 12 with the elongated body assembly 14, described hereinbelow.

Figure 8:
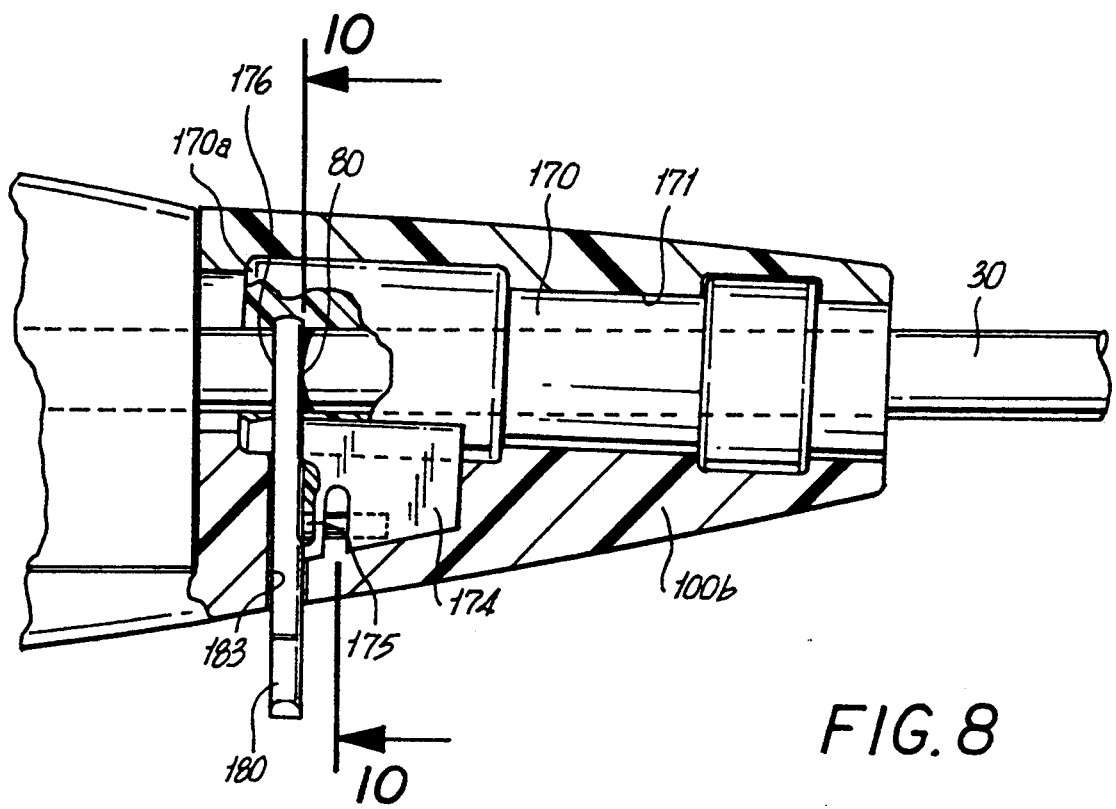
FIG. 8 is an enlarged side elevational view in partial cross-section of the distal end portion of the handle assembly illustrated in FIG. 4, wherein the locking mechanism is engaged with the proximal end portion of the outer tubular member.

Referring to FIGS. 4 and 8, the locking assembly 24 includes a drive tube member 170 mounted in the distal end portion 100b of the body 100 of the handle assembly 12. The drive tube member 170 defines a bore 171 therethrough dimensioned and configured for slidable reception of the distal end portion 30a of the outer tubular member 30.

A latch block member 174 is mounted beneath the proximal end portion 170a of the drive tube member 170 in the body portion 100 of the handle assembly 12 and includes a locking rod 175 projecting proximal from the latch block member 174 and in alignment with a locking cutout portion 176 defined in the proximal end portion 170a of the drive tube member 170. The locking cutout portion 176 is positioned on the proximal end portion 170a of the drive tube member 170, such that, the locking channels 80 and 82 (FIG. 2) of the outer tubular member 30 are in alignment with the locking cutout portion 176 when the proximal end portion 30a of the outer tubular member 30 is slidably received within the bore portion 171 of the drive tube member 170. A fiat latch member 180 fits into the locking cutout portion 176 and locking channels 80 and 82 so as to engage the outer tubular member 30 to the drive tube member 170 in the body portion 100 of the handle assembly 12.

The fiat latch member 180 includes a U-shaped top portion 182 configured to fit through a slot 183 defined on the bottom surface of the body portion 100 and into the locking cutout portion 176 of the drive tube member 170 and the locking channels 80 and 82 of the outer tubular member 30. Further, the U-shaped top portion 182 of the fiat latch member 180 fits into a snap-fit arrangement with the locking rod 175. The procedure to engage and disengage the outer tubular member 30 with the handle assembly 12, in view of the locking assembly 24, will be described hereinbelow.

Figure 10:
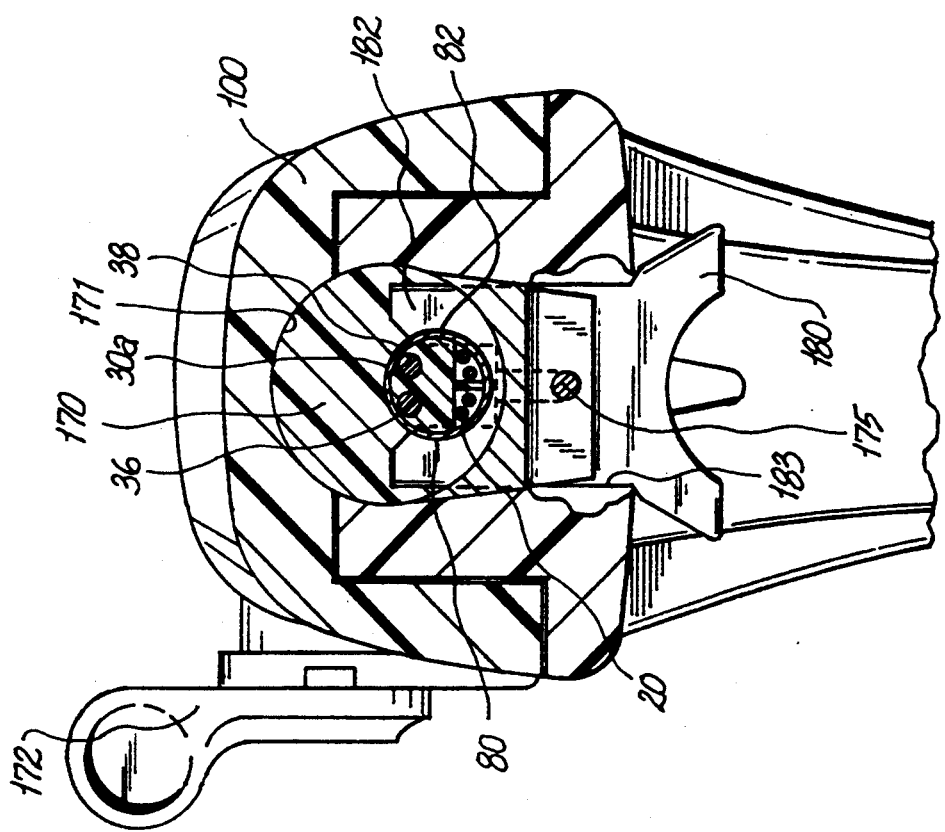
FIG. 10 is a cross-sectional view taken along line 10—10 of FIG. 8.

Referring to FIGS. 8 and 10, to connect the elongated body assembly 14 to the handle assembly 12, the proximal end portion 30a of the outer tubular member 30 is slidably received into the bore portion 171 of the drive tube member 170, such that, the locking channels 80 and 82 of the outer tubular member 30 are in alignment with the locking cutout portion 176 of the drive tube member 170. As mentioned above, the U-shaped top portion 182 of the fiat latch member 180 is received through the slot 183 on the bottom surface of the body portion 100 and moved into a snap-fit arrangement with the locking rod 175, whereby the U-shaped top portion 182 of the pin member 180 is received in the locking cutout portion 176 of the drive tube member 170 and through the locking channels 80 and 82 of the outer tubular member 30. Thus, the fiat latch member 180 restrains longitudinal movement of the outer tubular member 30 with respect to the handle assembly 12, such that, the first and second elongated needle members 36 and 38 may operatively interact with the drive arm member 114 in the handle assembly 12, via the switching mechanism 22 (FIG. 4).

Figure 9:
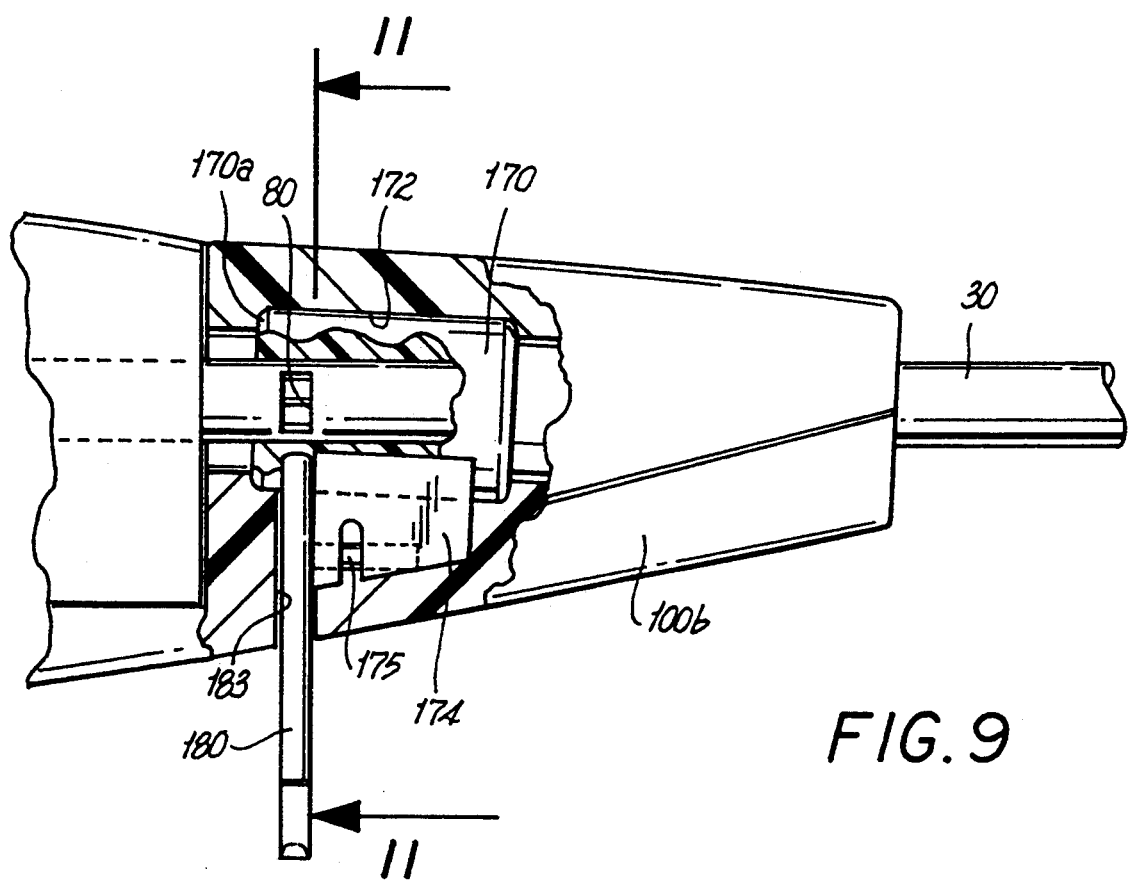
FIG. 9 is an enlarged side elevational view in partial cross-section of the distal end portion of the handle assembly wherein the locking mechanism is disengaged from the proximal end portion of the outer tubular member.
Figure 11:
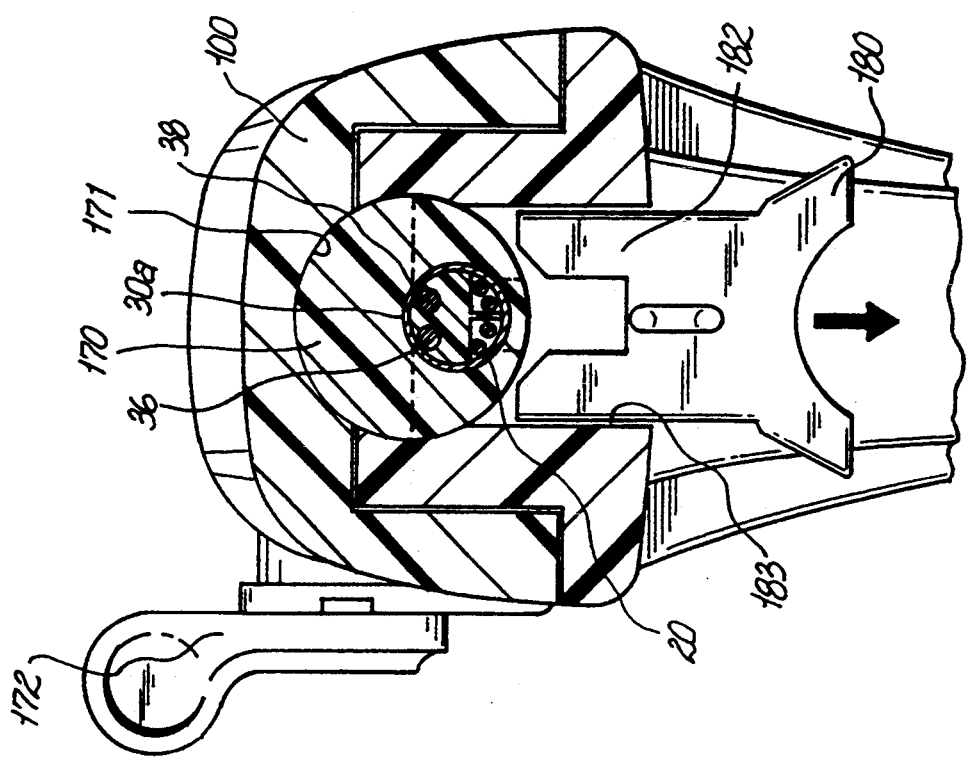
FIG. 11 is a cross-sectional view taken along line 11—11 of FIG. 9.

Referring to FIGS. 9 and 11, to disengage the elongated body assembly 14 from the handle assembly 12, the fiat latch member 180 is pulled downward relative to the body portion 100 by pulling on side wings 181, thereby effecting the U-shaped top portion 182 of flat latch member 180 to disengage from the snap-fit arrangement with the locking rod 175. Thus, when flat latch member 180 is pulled down from the body portion 100 of the handle assembly 12, the outer tubular member 30, housing all the components of the elongated body assembly 14, may be slidably removed and separable from the handle assembly 12 via the drive tube member 170.

In another embodiment, the outer tubular member 30 and the elongated insert member 37 of the elongated body assembly are permanently attached to the handle section 100. A disposable loading unit is made up of the suture 20, a plastic tube that holds the suture (not shown), ferrules 16 and 18 and two short needles that are all contained in a plastic tip. Thus, elongated needles 36 and 38 are replaced with shorter needles and needle drivers, these shorter needles being releasably attached to the needle drivers. The ferrules remain attached to the short needles after the instrument is fired. The needles and attached ferrules are removed from the body cavity after the instrument has been fired.

In a further embodiment wherein the outer tubular member 30, and the elongated insert member 37 are permanently attached to handle section 100, a disposable loading unit is made up of the suture 20, a plastic tube that holds the suture (not shown) and ferrules 16 and 18 contained in a plastic tip located at the end of elongated insert member 37. The needles 38 and 36 are positioned in insert member 37. The ferrules in this embodiment are releasably engaged to the needles after firing the instrument so that the ferrules can be pulled off the needles when the disposable loading unit is removed from the instrument. In this embodiment, the holding force of the suture to the ferrule would exceed the holding force of the ferrule to the needle.

In another embodiment, the tissue receiving portion of the instrument may be articulated as follows. The needles 36 and 38 contain a section of memory metal or other flexible material to allow passage of the articulated joint. In such "passive articulation", the distal end portion 30b is attached to the outer tubular member 30 with a section of memory metal or other suitable material, pre-bent to the desired angle. The action of inserting the instrument or withdrawing it from the cannula will straighten the instrument so that it fits through the cannula.

In another such embodiment, the distal end portion 30b is articulated, and the needles 36 and 38 contain a section of memory metal or other flexible material to allow passage through the articulated joint. In this "active articulation" embodiment, however, the distal end portion 30b is attached to the outer tubular member 30 with a hinged joint and can be actuated by the handle. A control rod or other mechanism is attached to the distal end portion of the outer tubular member. When actuated, this mechanism moves through its range of articulation.

With all the components of the surgical apparatus 10 of the present invention being fully described above, the method of use of the surgical apparatus 10 of the present invention will now be fully described hereinbelow.

First, as fully described above, the surgeon connects an elongated body assembly 14 to the handle assembly 12 through manipulation of the locking assembly 24. Alternately, the instrument can be packaged with the elongated body assembly 14 detachably connected to handle assembly 12. First and second ferrule portions 16 and 18 connected to the opposing ends of a length of suture material 20 are releasably retained in the distal end portion 30b of the outer tubular member 30 (FIG. 2).

Figure 12:
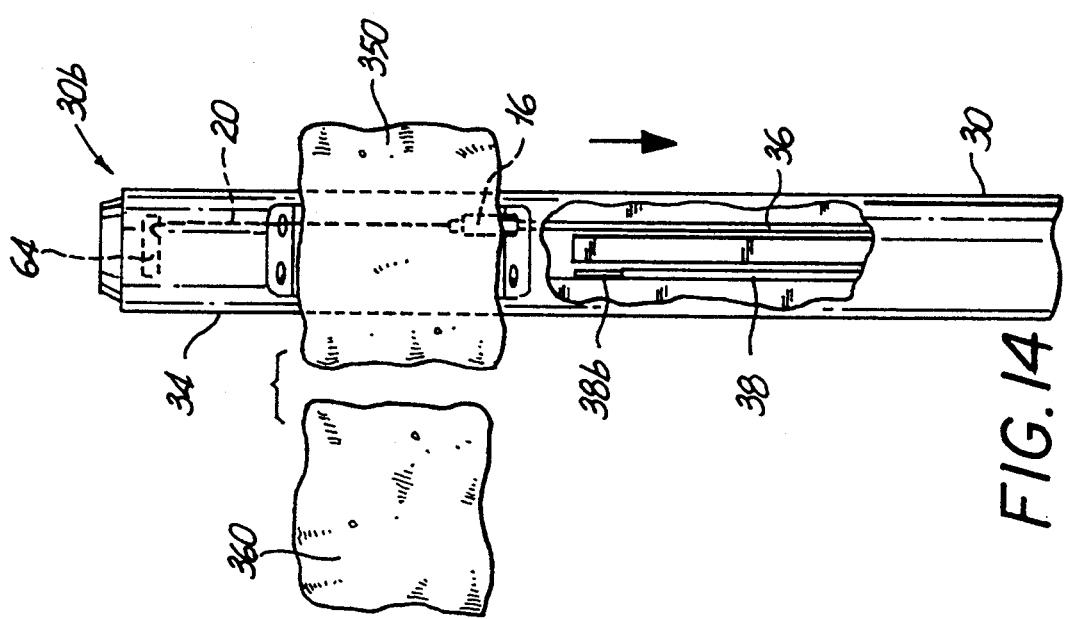
FIG. 12 is a top elevational view in partial cutaway of the distal end portion of the elongated body assembly illustrated in FIG. 2, wherein a first tissue piece is received in the tissue receiving portion of the elongated body assembly.

Referring now to FIGS. 12-17 in conjunction with FIG. 1, the surgeon introduces the distal end portion 30b of the outer tubular member 30 of the surgical apparatus 10 into the body cavity, via a cannula assembly (not shown), The surgeon may then position the switching mechanism 22 to the first position so as to engage the proximal end portion 36a of the first elongated needle member 36 with the drive arm member 114 of the handle assembly 12 (FIG. 5). The surgeon then, through manipulation of the surgical apparatus 10, positions a first tissue piece 350 into the tissue receiving portion 34 defined at the distal end portion 30b of the outer tubular member 30 (FIG. 12).

Figure 13:
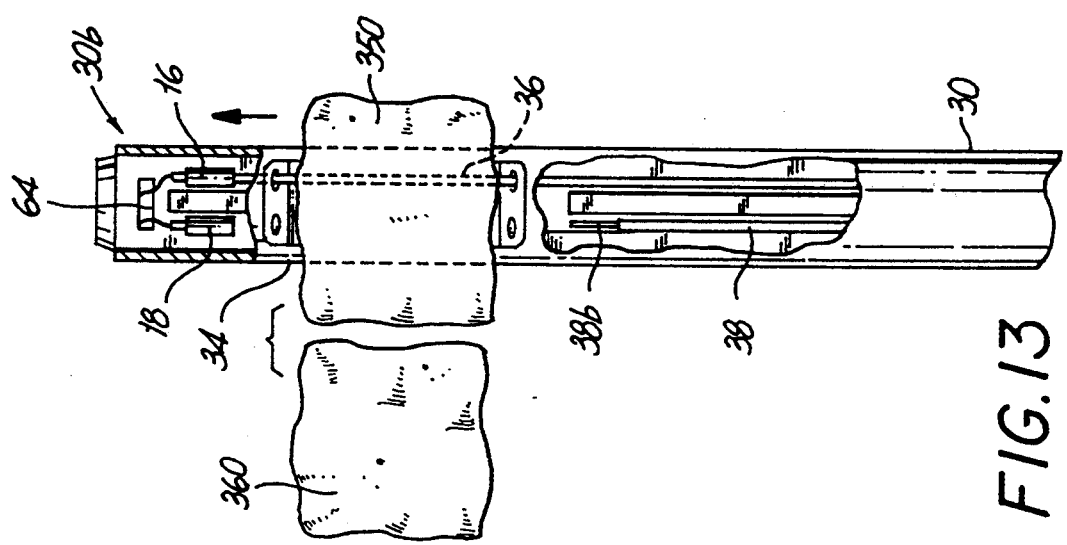
FIG. 13 is a top elevational view in partial cutaway of the distal end portion of the elongated body assembly illustrated in FIG. 12, wherein the first elongated needle member has pierced through the first tissue piece and engaged a first ferrule portion.
Figure 14:
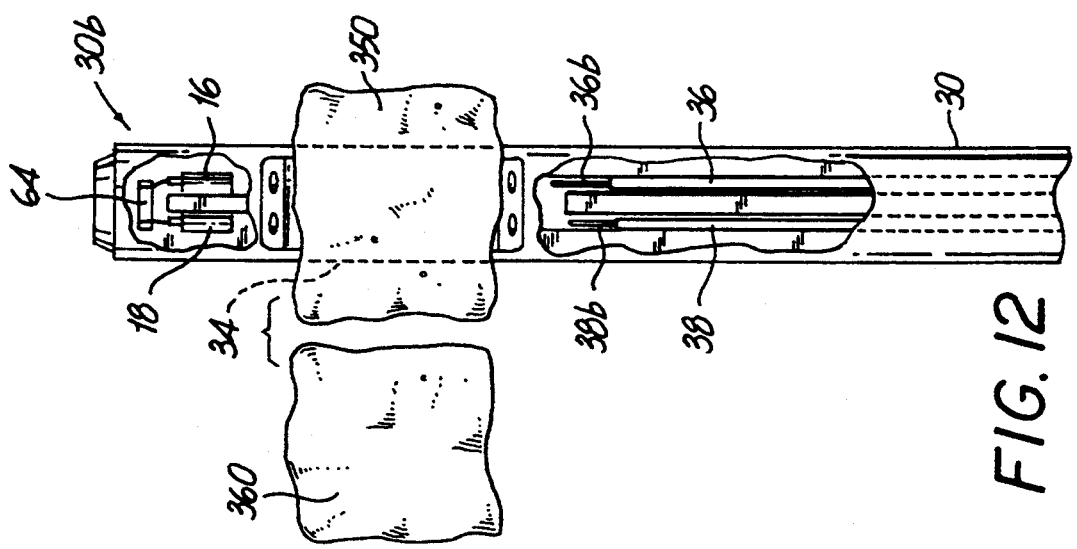
FIG. 14 is a top elevational view in partial cutaway of the distal end portion of the elongated body assembly illustrated in FIG. 13, wherein the first ferrule portion and attached length of suture material have moved proximally through the first tissue piece.

Next, the surgeon actuates the pivotable handle member 106 effecting reciprocating movement of the drive arm member 114, which in turn, effects corresponding reciprocating coaxial movement of the first elongated needle member 36 in the outer tubular member 30 between a distal and proximal position. During distal movement, the sharpened distal end 36b of the first elongated needle member 36 pierces through the first tissue piece 350 received in the tissue receiving portion 34 and engages the first ferrule portion 16 releasably retained in the distal end 30b of the outer tubular member 30 (FIG. 13). During proximal movement effected by release of pivotable handle member 106, the sharpened distal end 36b of the first elongated needle member 36 reciprocates back into the first tissue piece 350 thereby pulling first ferrule portion 16 through the first tissue piece 350. Thus, the first end of suture 20 passes through the first tissue piece 350.

Next, the surgeon positions the switching mechanism 22 to the second position so as to engage the proximal end portion 38a of the second elongated needle member 38 with the drive arm member 114 in the handle assembly 12 (FIG. 6). The surgeon then, through further manipulation of the surgical apparatus 10, moves the distal end portion 30b of the outer tubular member 30 away from the first tissue piece 350 and introduces a second tissue piece 360 into the tissue receiving portion 34 at the distal end portion 30b of the outer tubular member 30 (FIG. 15).

Still referring to FIG. 15, the surgeon passes the second end of suture 20 through the second tissue piece 360 by movement of pivotable handle member 106 towards stationary grip 114 as described above, so as to drive elongated needle member 38 into second ferrule portion 18. The handle is then released, pulling the needle member 38 and attached ferrule portion 18 through the second tissue piece 360. The surgeon then moves the distal end portion 30b of the outer tubular member 30 away from the first and second tissue pieces 350 and 360 causing the length of suture material 20 to release from the elongated body assembly 14, via the aperture 64 defined at the distal end 37b of the elongated insert member 37 (FIG. 17).

At this point, the surgeon puts suture 20 under tension, thereby bringing tissue pieces 350 and 360 together and, in some embodiments, securing suture 20 with the novel cinch members described in copending application Ser. Nos. 08/201,864 entitled Surgical Crimping Device and Method of Use, filed Feb. 24, 1994, and 08/201,289 entitled Method and Apparatus for Applying a Cinch Member to the Ends of a Suture, filed Feb. 24, 1994. Alternately, the suture end can be tied or tensioned using other conventional techniques. While ferrules 16 and 18 are still engaged with needles 36b and 38b, suture 20 is cut near ferrules 16 and 18, thereby releasing the suture from the ferrules. Needle 36b and 38b, still attached to ferrules 16 and 18, are withdrawn from the body cavity.

Finally, the surgeon removes the distal end portion 30b of the outer tubular member 30 from the body cavity, via a cannula assembly. If the surgeon desires to apply another suture, he can disengage the elongated body assembly 14 from the handle assembly by first positioning the switching mechanism 22 to the third position (FIG. 7) and then pulling fiat latch member 180 down from the body portion 100 of the handle assembly 12 (FIG. 9). A new elongated body assembly 14 having first and second ferrule portions 16 and 18 connecting to a length of suture material 20 is then connected to the handle assembly 12 as described above. The surgeon is then prepared to repeat the above described method.

Referring now to FIG. 18, an example of an instrumentation kit which can be used is designated generally at 200. The preferred embodiment of the kit 200 includes the surgical apparatus 10 having a handle assembly 12 connected to an elongated body assembly 14 extending therefrom. At least one more additional elongated body assembly 14 configured for detachable engagement with the handle assembly 14 of the surgical instrument 10 is provided in the instrumentation kit 200. It is to be appreciated that a multiplicity of body assemblies 14 may be provided in each instrumentation kit 200 for each surgical instrument 10 provided therein. The surgical instrument 10 and the at least one elongated body assembly 14 are contained in a package which includes a first cover 202 fabricated of a planar material such as Tyvek ®, which provides for sterilization after packaging, and a second vacuum-formed plastic cover 204 which encloses and displays the surgical instrument 10 and at least one elongated body assembly 14. The vacuum-formed cover provides recesses 210 which correspond substantially in shape and dimension in cooperation with the surgical apparatus 10 and the at least one elongated body assembly 14 packaged therein. Additionally, at least one of the covers is preferably transparent to provide an unobstructed view of the instrumentation packaged therein.

While the invention has been particularly shown and described with reference to the preferred embodiments, it will be understood by those skilled in the art that various modifications in form and detail may be made therein without departing from the scope and spirit of the invention. Accordingly, modifications such as those suggested above, but not limited thereto, are to be considered within the scope of the invention.

What is claimed is:

1. A surgical suturing apparatus comprising:
   a) a handle assembly;
   b) an elongated body assembly extending from said handle assembly;
   c) first and second needle receiving portions positioned at a distal end portion of the apparatus and interconnected by a length of flexible material;
   d) an actuating mechanism for pulling said needle receiving portions proximally through body tissue, said actuating mechanism operably connected to said handle assembly and engageable with said first and second needle receiving portions.

2. A surgical suturing apparatus as recited in claim 1, wherein said elongated body assembly is detachably connected to said handle assembly.

3. A surgical suturing apparatus as recited in claim 2, further comprising a locking assembly operably connected to said handle assembly for detachably securing the handle assembly and said elongated body assembly.

4. A surgical suturing apparatus as recited in claim 1, wherein said elongated body assembly includes an outer tubular member, said outer tubular member having a cutout portion in proximity to a distal end thereof for receiving body tissue.

5. A surgical suturing apparatus as recited in claim 1, wherein said actuating mechanism includes first and second elongated needle members positioned within said elongated body assembly for reciprocating coaxial movement.

6. A surgical suturing apparatus as recited in claim 5, wherein said first and second elongated needle members are positioned in parallel relationship to one another and said needle receiving portions are releasably retained in a distal end portion of said elongated body assembly.

7. A surgical suturing apparatus as recited in claim 6, wherein said handle assembly includes a pivotable handle member and a drive arm member operably connected to said pivotable handle member, said drive arm member configured to engage a proximal end portion of each said first and second elongated needle members so as to effectuate reciprocating coaxial movement of each of said respective needle members.

8. A surgical suturing apparatus as recited in claim 7, further including a switching mechanism operable from said handle assembly for providing selective engagement between said drive arm member and each said first and second elongated needle member.

9. A surgical suturing apparatus as recited in claim 5, wherein said first and second needle-receiving portions each define a longitudinal bore dimensioned to frictionally engage the first and second elongated needle members.

10. A surgical suturing apparatus comprising:
a) an elongated body assembly;
b) a suture positioned in the body assembly;
c) at least one needle positioned in the body assembly and movable from a first position spaced from the suture to a second position connected with the suture; and
an actuating mechanism positioned at a proximal end of said elongated assembly, the actuating mechanism moveable from a first position to a second position to move the at least one needle from the first position to the second position to engage the suture.

11. A surgical suturing apparatus as recited in claim 10, wherein said elongated body assembly is detachably connected to said actuating mechanism.

12. A surgical suturing apparatus as recited in claim 10, further comprising two elongated needles positioned parallel to one another within the elongated body assembly.

13. A surgical suturing apparatus as recited in claim 10, wherein said actuating mechanism comprises a handle assembly connected to said elongated body assembly.

14. A surgical suturing apparatus as recited in claim 10, wherein said elongated body assembly further includes an elongated insert member received in an outer tubular member, said elongate insert member defining elongated substantially parallel first and second elongated guide channels along said longitudinal axis of said elongated body assembly.

15. A surgical suturing apparatus as recited in claim 10, wherein said suture has first and second needle receiving portions attached to respective first and second ends of said suture and the at least one needle engages the suture by engaging the needle receiving portions.

16. A surgical suturing apparatus as recited in claim 10, wherein said elongated body assembly includes at least one cutout portion in proximity to a distal end thereof for receiving body tissue.

17. A surgical suturing apparatus as recited in claim 15, wherein said needle receiving portions are substantially cylindrical in configuration and define a longitudinal bore therein to receive said needles.

18. A surgical suturing apparatus as recited in claim 17, wherein said needle receiving portions are comprised of flexible material.

19. A method of endoscopically suturing body tissue comprising the steps of:
a) inserting into a body cavity a distal end portion of a surgical apparatus having a first end of suture and a second end of suture;
b) positioning said distal end portion of said surgical apparatus adjacent a first body tissue portion such that the first body tissue portion is positioned between the first end of suture and a proximal portion of the apparatus;
c) piercing said first body tissue portion and pulling said first end of suture proximally through said first body tissue portion;
d) subsequently positioning said distal end portion of said surgical apparatus adjacent a second body tissue portion without removing said apparatus from the body cavity such that the second body tissue portion is positioned between the second end of suture and the proximal portion of the apparatus and;
e) piercing said second body tissue piece and pulling said second end of said suture proximally through said second body tissue portion.

20. The method of endoscopically suturing body tissue of claim 19, wherein the step of pulling the first and second ends of surgical suture comprises the step of engaging a ferrule attached to each end of the suture.

21. The method of endoscopically suturing body tissue of claim 20, wherein the step of pulling the first and second ends of surgical suture comprises moving a pair of needles disposed in said surgical apparatus into engagement with the ferrules.

* * * * *